United States Patent [19]

Kallenbach et al.

[11] Patent Number: 5,427,689

[45] Date of Patent: Jun. 27, 1995

[54] SEPARATION OF POLAR SUBSTANCES FROM HYDROCARBONS

[75] Inventors: Lyle R. Kallenbach; Marvin M. Johnson, both of Bartlesville, Okla.

[73] Assignee: Phillips Petroleum Company, Bartlesville, Okla.

[21] Appl. No.: 323,562

[22] Filed: Oct. 17, 1994

[51] Int. Cl.$^6$ ................................................. C02F 1/28
[52] U.S. Cl. ..................................... 210/670; 210/689; 210/690; 208/299; 208/305; 208/306; 585/820; 585/823; 585/824
[58] Field of Search ............... 210/689, 690, 681, 670, 210/660; 208/299, 305, 306; 585/823, 824, 820

[56] References Cited

U.S. PATENT DOCUMENTS

| | | | |
|---|---|---|---|
| 2,137,605 | 11/1938 | Derr | 210/689 |
| 3,922,217 | 11/1975 | Cohen et al. | 210/690 |
| 4,034,061 | 7/1977 | McArthur | 423/213.5 |
| 4,952,550 | 8/1990 | Wallach et al. | 502/404 |
| 4,968,655 | 11/1990 | Jezl et al. | 502/242 |

OTHER PUBLICATIONS

M. C. Tsai and Y. W. Chen, "Hydrothermal Stability of Aluminum Borate", Catalysis Letters 6, (1990), pp. 225–230.

*Primary Examiner*—Cynthia L. Nessler
*Attorney, Agent, or Firm*—K. K. Brandes

[57] ABSTRACT

A process for separating polar substances (preferably water, alcohols, ethers, aldehydes, nitriles) from hydrocarbon fluids employs a sorbent comprising aluminum borate and zirconium borate. Preferably, the sorbent composition has been prepared by coprecipitation.

13 Claims, No Drawings

SEPARATION OF POLAR SUBSTANCES FROM HYDROCARBONS

BACKGROUND OF THE INVENTION

This invention relates to use of a metal borate composition as a sorbent for removing polar compounds from hydrocarbons (these polar compounds are present as impurities). The sorbent composition used in the separation process of the present invention is more effective than alumina.

SUMMARY OF THE INVENTION

It is an object of this invention to employ a novel borate composition as a sorbent material in a process for separating polar substances from hydrocarbons.

In accordance with this invention, a process for removing polar substances from hydrocarbon-containing fluids comprises contacting a fluid feed comprising at least one hydrocarbon containing 1–10 carbon atoms per molecule and at least one polar substance selected from the group consisting of water, alcohols, ethers, aldehydes, ketones, amines, mercaptans, organic sulfides, carboxylic acids, carboxylic acid anhydrides, carboxylic acid amides, esters and nitriles with an effective sorbent composition at effective contacting conditions so as to form a product containing less of said at least one polar organic substance than said feed, wherein the sorbent composition comprises aluminum borate and zirconium borate.

Preferably, the sorbent composition has been prepared by a method which comprises adding an alkaline solution to an aqueous solution comprising at least one aluminum salt, at least one zirconium salt and at least one boric acid so as to raise the pH of the aqueous solution sufficiently to form a coprecipitate comprising aluminum borate and zirconium borate, separating the formed coprecipitate from the aqueous solution, drying the separated coprecipitate, and calcining the dried coprecipitate at a temperature of about 450°–550° C.

DETAILED DESCRIPTION OF THE INVENTION

The metal borate composition comprising aluminum borate and zirconium borate employed in the separation process of this invention generally has a weight ratio of Al to Zr in the range of about 2:1 to about 20:1 (preferably about 4:1 to about 12:1) and a weight ratio of (Al+Zr) to B in the range of about 1:1 to about 6:1 (preferably about 1.5:1 to about 3:1). Generally, this composition has a surface area (measured by the BET method employing $N_2$) of about 150 to about 350 $m^2/g$ and a pore volume (measured by a pore size distribution method employing $N_2$) of about 0.2 to about 1.5 cc/g. The particles of this composition can have any suitable shape (spherical, cyclindrical, trilobal or irregular) and can have any suitable particle size (preferably about 0.4–0.8 mm). When these particles have been compacted and extruded, the formed cylindrical extrudates generally have a diameter of about 1–4 mm and a length of about 3–10 mm. Preferably, the sorbent composition consists essentially of borates of Al and Zr. However, it is within the scope of this invention to have minor amounts of aluminum oxide and zirconium oxide (generally about 1–5 weight-% of each) present in this composition.

Preferably, the metal borate composition which is employed in the separation process of this invention is prepared by coprecipitation. First, an aqueous solution containing any water-soluble, non-hydrolyzable aluminum salt (preferably aluminum nitrate), any water-soluble, non-hydrolyzable zirconium salt (preferably zirconyl nitrate) and any water-soluble, non-hydrolyzable, acidic boron compound (preferably a boric acid, more preferably $H_3BO_3$) is prepared. Any suitable concentrations of these compounds in the aqueous solution can be employed (generally about 0.02–1 mole/l of each, depending on the desired Al:Zr:B ratio). Generally, the initial pH of this aqueous solution is about 1–3. Then an alkaline solution (preferably an aqueous solution of ammonia containing about 25–28 weight-% $NH_3$), generally having a pH of 10–14, is added to the first aqueous solution in an amount sufficient to raise the pH of the first solution to above 7, preferably to about 8–9, so as to afford the coprecipitation of borates of aluminum and zirconium. The dispersion of the formed coprecipitate in the aqueous solution is then subjected to any suitable solid-liquid separation (preferably filtration) so as to substantially separate the coprecipitate from the aqueous solution. Preferably, the coprecipitate is washed with water (to remove adhered solution therefrom), optionally followed by washing with a water-soluble organic solvent such as methanol, ethanol, isopropanol (preferred), acetone and the like. The washed coprecipitate is generally dried (preferably in a vacuum oven at a temperature of about 110°–180° C., for about 2–16 hours), and is then calcined (preferably in air at a temperature of about 450°–550° C. for about 3–16 hours). It is within the scope of this invention to mix the formed metal borate coprecipitate with an effective binder material (such as a polyglycol, a polyoxazoline or carbon black) which is substantially burned off during the calcining step. It is also within the scope of this invention to extrude or pelletize the metal borate coprecipitate (with or without a binder) before the calcination.

The separation process of this invention can be carded out in any suitable manner which affords the removal of polar substances from hydrocarbon streams (preferably liquid streams). Generally, the hydrocarbon(s) contained in the feed stream can be any hydrocarbon (alkane, cycloalkane, alkene, aromatic hydrocarbon) which contains 1–10 carbon atoms per molecule (preferably 4–8 C atoms per molecule) or mixtures of two or more of these hydrocarbons. Presently preferred feed hydrocarbons are butanes (n-butane, isobutane), pentanes (n-pentane, isopentanes), butenes (butene-1, butene-2, isobutylene), pentenes (pentene-1, pentene-2, isopentenes) and mixtures of the above hydrocarbons.

The hydrocarbon feeds used in the process of this invention generally contain minor amounts of polar substances (i.e., less than about 50 weight percent of the feed). Suitable polar substances which are present in the feed can be any one or two or more than two of the following: water, alcohols, ethers, aldehydes, ketones, amines, mercaptans, organic sulfides, carboxylic acids, carboxylic anhydrides, carboxylic acid amides, esters and nitriles. Examples of these polar substances include (but are not limited to) methanol, ethanol, propanol, glycol, dimethyl ether, methyl ethyl ether, diethyl ether, formaldehyde, acetaldehyde, benzaldehyde, acetone, methyl ethyl ketone, benzophenone, methylamine, dimethylamine, trimethylamine, ethylamine, diethylamine, methylethylamine, methyl mercaptan, dimethyl sulfide, dimethyl disulfide, formic acid, acetic acid, propionic acid, maleic acid, benzoic acid, acetic anhydride, propionic anhydride, maleic anhydride, benzoic anhydride, acetamides, acetonitrile, and mixtures of any of the above polar substances. Presently preferred polar substances are water, alkyl alcohols (more preferably methanol, ethanol, dialkyl ethers (e.g., diethyl ether) alkyl aldehydes (more preferably acetaldehyde), dialkyl ketones (more preferably acetone) and alkyl nitriles (more preferably acetonitrile). Frequently, the polar substances present in the hydrocarbon feed stream are present as impurities in the range of about 1 ppm (1 part by weight per million parts by weight of feed) to about 1 weight percent.

The separation process of this invention can be carried out in any suitable manner which will result in the separation (removal) of at least a portion (preferably a major portion) of the polar substance(s) from the hydrocarbon(s) which are present in the feed. Generally, the feed is liquid at the contacting conditions of the separation process. The process can be carried out in a batch mode (generally with agitation) or in a continuous flow mode. In a continuous process, the feed is passed (preferably in a downflow mode) through a bed (layer) containing the solid metal borate sorbent (described above). Any effective contacting conditions can be applied so as obtain a liquid product which contains a smaller concentration of the polar substances (also referred to as polar impurities) than the liquid feed. Effective contacting conditions comprise a temperature of about 20°–40° C., an absolute pressure of about 2–4 atm, and a contacting time of about 1 minute to about 20 hours. In a continuous flow process, the liquid hourly space velocity is generally about 40–100 cc liquid feed per cc sorbent composition (comprising Al Zr borate) per hour. When the maximum sorption capacity of the sorbent composition has been reached, the spent sorbent composition can be regenerated by heating it to an elevated temperature (generally about 200°–300° C., preferably at about 230°–250° C.) for a sufficient time to drive off absorbed/adsorbed polar substances therefrom. The thus-regenerated sorbent composition can be reused in the separation process of this invention.

The following examples are presented to further illustrate the present invention and are not to be construed as unduly limiting the scope of this invention.

Example I

This example illustrates the preparation of an aluminum zirconium borate composition in accordance with a preferred preparation method.

Composition A was prepared as follows: 13.75 grams (0.05 mole) of $ZrO(NO_3)_2.2 H_2O$ (formula weight: 267) and 220.9 grams (0.59 mole) of $Al(NO_3)_3.9H_2O$ (formula weight: 375) were mixed with 48.1 grams (0.78 mole) of $H_3BO_3$ (orthoboric acid; formula weight: 62) and 1.5 liters of distilled water. The mixture was heated until all solids were dissolved. Then 31.4 grams of a binder additive, which contained 8.0 weight-% of poly(2-ethyl-2-oxazoline) (PEOZ, available as "Dow Binder" from Dow Chemical U.S.A., Midland, Mich.), 2.8 weight-% of poly(ethylene glycol) (PEG; molecular weight:300; available from Aldrich Chemical Company, Milwaukee, Wis.) and isopropanol as the remainder, was added to the mixture with stirring. Thereafter, an aqueous ammonia solution (containing 28 weight-& $NH_3$) was added to the entire mixture (pH: about 2) until a pH of about 8 was attained and an Al-Zr-borate coprecipitate was formed. A second batch of Al-Zr-borate was prepared essentially in accordance with the above procedure. Both batches were combined and filtered. The combined filter cake was washed with about 1.5 liter of distilled water and then with 1.5 liter of isopropanol. The solid filter cake was dried at 150° C. overnight in a vacuum oven, followed by calcining at 500° C. (so as to burn off the added polymeric binders). The calcined material had a surface area (measured by the BET method using $N_2$) of 295 $m^2/g$ and a pore volume (measured by a $N_2$ pore size distribution method) of 0.36 $cm^3/g$. It contained 30.0 weight-% Al, 8.4 weight-% Zr and 11.0 weight-% B.

Composition B was essentially prepared in accordance with the procedure for Composition A, except that no binder additive had been added. The surface area of this material was 187 $m^2/g$, and the pore volume was 1.22 $cm^3/g$.

Both compositions were ground and sieved. A 20–40 mesh fraction of Composition B was retained for further testing.

Example II

This example illustrates the use of a coprecipitated Al-Zr-borate composition (described in Example I) for absorbing various polar organic substances from dilute solutions of these substances in a liquid alkane.

Four dilute solutions were prepared and tested: (a) 1 mL methanol +99 mL n-pentane; (b) 1 mL ethanol +99 mL n-pentane; (c) 1 mL acetone +99 mL n-pentane; and (d) 1 mL acetaldehyde +99 mL n-pentane. The following solid sorbents were used in the absorption tests: a 20–40 mesh fraction of Composition B (Al-Zr-borate) and a 20–40 mesh fraction of alumina (surface area: 210 $m^2/g$; pore volume: 0.4 $cm^3/g$). Both materials had been calcined at about 500° C. in air for about 16 hours and were then allowed to cool.

About 4 mL of each of the four solutions was mixed with 2 grams of each of the two sorbents. Each mixture was placed in a sealed ampoule which was shaken overnight at about 30° C. Thereafter, each solution was analyzed by means of a gas chromatograph to determine the amount of the particular polar solute (methanol, ethanol, acetone or acetaldehyde) which remained in the n-pentane solution after it had been contacted with Al-Zr-borate (Composition B) and alumina, respectively. Test results are summarized in Table I.

TABLE I

| Sorbent | Sorbate | % Removal n- Pentane Solution |
|---|---|---|
| Al-Zr-Borate (Invention) | Methanol | 91.0 |
| Al-Zr-Borate (Invention) | Ethanol | 93.6 |
| Al-Zr-Borate (Invention) | Acetone | 82.9 |
| Al-Zr-Borate (Invention) | Acetaldehyde | 96.7 |
| Alumina (Control) | Methanol | 74.3 |
| Alumina (Control) | Ethanol | 58.4 |
| Alumina (Control) | Acetone | 76.3 |
| Alumina (Control) | Acetaldehyde | 95.3 |

Test data in Table I clearly show that the composition containing coprecipitated aluminum borate and zirconium borate adsorbed more of each polar organic substance than conventional alumina. An additional test showed that adsorbed methanol could be quantitatively removed from Al-Zr-borate by heating at about 240° C. for about 2 hours, thus indicating the regenerability of this sorbent composition.

A further test indicated that Al-Zr-borate reacted with water (probably to form a hydrate) and generated more heat of immersion than alumina. Based on this result, it is concluded that Al-Zr-borate absorbs more water than alumina.

Example III

This example further illustrates the effectiveness of Al-Zr-borate as a sorbent material for polar organic substances dissolved in a liquid hydrocarbon.

A "butane/butylene" stream from a Phillips Petroleum Company refinery contained about 12.4 weight-% n-butane, about 24.9 weight-% of isobutane, about 25.6 weight-% of 1-butenes (n-butene-1, isobutylene), about 25.8 weight-% 2-butenes (cis- and trans-butene-2), about 8.0 weight-% pentanes (n- and iso-pentane), about 3.2 weight-% of pentenes, about 130 ppm acetone (i.e., 130 parts by weight of acetone per million parts by weight of feed), 3 ppm methanol and 3 ppm acetonitrile.

This refinery stream was pumped through a glass-lined stainless steel column containing a bottom layer of 8.3 grams of Alundum ® (inert alumina having a surface area of less than 1 m$^2$/g, having been calcined at 500° C. for 18 hours), a middle layer of 7.7 grams of calcined, 20–40 mesh Al-Zr-borate, and a top layer of 14.3 grams of Alundum ®, at a temperature of about 30° C. After 6.5 hours, the test run was stopped and the effluent was analyzed. Result: the product contained less than 1 ppm methanol, less than 1 ppm acetonitrile, and about 36 ppm acetone. Thus, a substantial portion of these polar impurities had been removed from the refinery stream.

Reasonable variations, modifications and adaptations for various usages and conditions can be made within the scope of the disclosure and the appended claims, without departing from the scope of this invention.

That which is claimed:

1. A process for removing polar substances from hydrocarbon-containing fluids which comprises contacting a fluid feed comprising at least one hydrocarbon containing 1–10 carbon atoms per molecule and at least one polar substance selected from the group consisting of water, alcohols, ethers, aldehydes, ketones, amines, mercaptans, organic sulfides, carboxylic acids, carboxylic acid anhydrides, carboxylic acid amides, esters and nitriles with a sorbent composition at effective contacting conditions so as to obtain a product containing less of said at least one polar substance than said feed, wherein said sorbent composition comprises aluminum borate and zirconium borate.

2. A process in accordance with claim 1, wherein said feed is contacted with said sorbent composition in a batch mode.

3. A process in accordance with claim 1, wherein said feed is contacted with said sorbent composition in a continuous flow mode.

4. A process in accordance with claim 1, wherein said contacting is carried out at a temperature of about 20°–40° C.

5. A process in accordance with claim 1, further comprising the step of regenerating said sorbent composition, after it has reached its maximum sorption capacity, by heating said sorbent composition to a temperature of about 200°–300° C.

6. A process in accordance with claim 1, wherein said at least one hydrocarbon contains about 4–8 carbon atoms per molecule, and said at least one polar substance is selected from the group consisting of water, alkyl alcohols, dialkyl ethers, alkyl aldehydes, dialkyl ketones and alkyl nitriles.

7. A process in accordance with claim 6, wherein said at least one hydrocarbon is selected from the group consisting of butanes, pentanes, butenes and pentenes.

8. A process in accordance with claim 6, wherein the concentration of said at least one polar substance in said feed is less than about 50 weight percent.

9. A process in accordance with claim 8, wherein said at least one polar substance is selected from the group consisting of water, methanol, ethanol, acetaldehyde, acetone and acetonitrile.

10. A process in accordance with claim 1, wherein the weight ratio of Al to Zr in said sorbent composition is in the range of about 2:1 to about 20:1 and the weight ratio of (Al+Zr) to B in said sorbent composition is in the range of about 1:1 to about 6:1.

11. A process in accordance with claim 10, wherein the weight ratio of Al to Zr is in the range of about 4:1 to about 12:1 and the weight ration of (Al+Zr) to B is in the range of about 1.5:1 to about 3:1.

12. A process in accordance with claim 10, wherein said sorbent composition has been prepared by a method comprising adding an alkaline solution to an aqueous solution comprising at least one aluminum salt, at least one zirconium salt and at least one boric acid so as to raise the pH sufficiently to form a coprecipitate comprising aluminum borate and zirconium borate, separating the formed coprecipitate from said aqueous solution, drying the separated coprecipitate, and calcining the dried coprecipitate at a temperature of about 450°–550° C.

13. A process in accordance with claim 10, wherein said composition has a surface area of about 150–300 m$^2$/g and a pore volume of about 0.2–1.5 cc/g.

* * * * *